(12) United States Patent
Ying et al.

(10) Patent No.: US 11,292,851 B2
(45) Date of Patent: Apr. 5, 2022

(54) SYNTHETIC PEPTIDE, RELATIVE ARTIFICIAL ANTIGEN, RELATIVE ANTI-EHD2 ANTIBODY AND PREPARATION METHOD THEREOF AND USE THEREOF

(71) Applicant: TIANJIN YINGSHIBO TECHNOLOGY DEVELOPMENT CO., LTD., Tianjin (CN)

(72) Inventors: Guoguang Ying, Tianjin (CN); Bo Liu, Tianjin (CN)

(73) Assignee: TIANJIN YINGSHIBO TECHNOLOGY DEVELOPMENT CO., LTD., Tianjin (CN)

( * ) Notice: Subject to any disclaimer, the term of this patent is extended or adjusted under 35 U.S.C. 154(b) by 314 days.

(21) Appl. No.: 16/292,054

(22) Filed: Mar. 4, 2019

(65) Prior Publication Data
US 2019/0241673 A1  Aug. 8, 2019

Related U.S. Application Data

(63) Continuation-in-part of application No. 15/301,259, filed as application No. PCT/CN2014/082480 on Jul. 18, 2014, now abandoned.

(30) Foreign Application Priority Data

Mar. 31, 2014 (CN) .................. 201410125627.X

(51) Int. Cl.
*C07K 16/30* (2006.01)
*C07K 7/04* (2006.01)
*G01N 33/574* (2006.01)
*G01N 33/58* (2006.01)
*C07K 16/18* (2006.01)
*C07K 14/47* (2006.01)
*A61K 39/00* (2006.01)

(52) U.S. Cl.
CPC ............ *C07K 16/3015* (2013.01); *C07K 7/04* (2013.01); *C07K 14/47* (2013.01); *C07K 16/18* (2013.01); *G01N 33/57415* (2013.01); *G01N 33/57492* (2013.01); *G01N 33/582* (2013.01); *A61K 2039/505* (2013.01); *A61K 2039/812* (2018.08); *C07K 2317/30* (2013.01); *C07K 2319/00* (2013.01); *G01N 2800/52* (2013.01)

(58) Field of Classification Search
CPC .... C07K 16/3015; C07K 16/18; C07K 14/47; C07K 7/04; C07K 2319/00; C07K 2317/30; G01N 33/57492; G01N 33/582; G01N 33/57415; G01N 2800/52; A61K 2039/505; A61K 2039/812
See application file for complete search history.

(56) References Cited

U.S. PATENT DOCUMENTS

| | | |
|---|---|---|
| 8,999,633 B2 | 4/2015 | Chin et al. |
| 2013/0315885 A1 | 11/2013 | Narain et al. |
| 2017/0145081 A1 | 5/2017 | Ying et al. |

FOREIGN PATENT DOCUMENTS

| | | |
|---|---|---|
| CN | 103923212 A | 7/2014 |
| EP | 1 347 046 A1 | 9/2003 |
| WO | 2008/048193 A2 | 4/2008 |

OTHER PUBLICATIONS

Current Protocols in Neuroscience 5.6.1-5.6.21 (1997).*
Jun. 18, 2019 Office Action issued in European Patent Application No. 14 887 836.6.
Dec. 3, 2019 Office Action issued in Japanese Patent Application No. 2016-560438, No English translation.
Jan. 17, 2020 Office Action issued in European Patent Application No. 14 887 836.6.
Pohl et al., "EHD2, EHD3, and EHD4 Encode Novel Members of a Highly Conserved Family of EH Domain-Containing Proteins," Genomics, 2000, vol. 63, pp. 255-262.
Translated Chinese Office Action in Chinese Application No. 2014010125627.X dated Jan. 13, 2016, a counterpart foreign application of U.S. Appl. No. 15/301,259, 5 pages.
Translated Chinese Office Action in Chinese Application No. 2014010125627.X dated Apr. 25, 2016, a counterpart foreign application of U.S. Appl. No. 15/301,259, 4 pages.
Translated Chinese Office Action in Chinese Application No. 2014010125627.X dated Jul. 15, 2016, a counterpart foreign application of U.S. Appl. No. 15/301,259, 4 pages.
Translated Chinese Office Action in Chinese Application No. 2014010125627.X dated Jul. 3, 2015, a counterpart foreign application of U.S. Appl. No. 15/301,259, 6 pages.
Guo et al., "EHD2 Regulation of the Polarity of Breast Mammary Epithelial Cells in 3D Culture", Chinese Journal of Clinical Oncology, Nov. 30, 2011 (Nov. 30, 2011), vol. 38, No. 11, ISSN: 1000-8179, translated. 11 pages.
Tian, Gang et al., "Down-regulation of EHD2 Enhanced Transformed Growth of Breast Epithelial Cell", Journal of Modern Laboratory Medicine, Jan. 31, 2012 (Jan. 31, 2012), vol. 27, No. 1, ISSN: 1671-7414. Translated 8 pages.
Wang, Hongyu et al., "Effects of EHD2 Interference on Proliferation and Migration of Immortalized Breast Epithelial Dells HBLIOO", Chinese Journal of Clinical Oncology, Nov. 30, 2011 (Nov. 30, 2011), vol. 38, No. 11, ISSN: 1000-8179. Translated 12 pages.

(Continued)

Primary Examiner — Alana Harris Dent
(74) Attorney, Agent, or Firm — Oliff PLC

(57) ABSTRACT

The present application provides a synthetic peptide with an amino acid sequence SEQ ID NO: 1 plus a cysteine at its N-terminal, an artificial antigen, an antibody specific to a human EHD2, a method for preparing an antibody specific to the human EHD2 protein and adopted to an immunohistochemical method for EHD2 detection as well as cancer diagnosing and prognosing.

4 Claims, 4 Drawing Sheets

Specification includes a Sequence Listing.

(56) References Cited

OTHER PUBLICATIONS

*Homo sapiens* EH domain containing 2 (EHD2), mRNA-Nucleotide-NCBI, GenBank No. AAF40470.1 (publicly available Mar. 10, 2000).
Translated Chinese Office Action in Chinese Application No. 2014010125627.X dated Nov. 17, 2016, a counterpart foreign application of U.S. Appl. No. 15/301,259, 9 pages.
Translated Chinese Office Action in Chinese Application No. 2014010125627.X dated Jun. 29, 2017, a counterpart foreign application of U.S. Appl. No. 15/301,259, 12 pages.
Anti-EHD2 Antibody (ab23935), A product summary, ABUKAMU, downloaded Oct. 2017, from http://www.abcam.co.jp/ehd2-antibody-ab23935.html. 3 pages.
Doherty et al., "The Endocytic recycling protein EHD2 interacts with myoferlin to regulate myoblast fusion," Jul. 2008 Journal of Biological Chemistry, 283(29):20252-20260.
Guilherme et al., "EHD2 and the novel EH domain binding protein EHBP1 couple endocytosis to the actin cytoskeleton," Dec. 2003. Journal of Biological Chemistry, 279(11): 10593-10605.
Translated Japanese Office Action in Japanese Application No. 2016-560438 dated Oct. 24, 2017, a counterpart foreign application of U.S. Appl. No. 15/301,259, 9 pages.
GenBank Accession No. NP 055416, Version NP_055416.2, Feb. 2, 2014 (Feb. 2, 2014), [Retrieved on Dec. 23, 2014 (Dec. 23, 2014)], Retrieved from NCBI [ online]: <URL: 4 http://www.ncbi.nlm.nih.gov/protein/NP055416>.
GenBank Accession No. NM 014601, Version NM_014601.3, Feb. 2, 2014 (Feb. 2, 2014), [Retrieved on Dec. 23, 2014 (Dec. 23, 2014)], Retrieved from NCBI [ online]: <URL: 4 http://www.ncbi.nlm.nih.gov/nuccore/I76866316>.
International Search Report dated Jan. 6, 2015 for corresponding PCT International Application No. PCT/CN2014/082480, 9 pages.
Jan. 6, 2015 Written Opinion issued in International Application No. PCT/CN2014/082480.
Dec. 1, 2017 extended Search Report issued in European Patent Application No. 14887836.6.
Sep. 25, 2018 Office Action issued in Japanese Patent Application No. 2016-560438.
Aug. 25, 2020 Office Action issued in Japanese Patent Application No. 2016-560438 (Appeal No. 2019-959), English translation provided.

\* cited by examiner

_US 11,292,851 B2_

SEQUENCE LISTING

```
<160> NUMBER OF SEQ ID NOS: 1

<210> SEQ ID NO 1
<211> LENGTH: 41
<212> TYPE: PRT
<213> ORGANISM: Artificial Sequence
<220> FEATURE:
<223> OTHER INFORMATION: Synthetic Sequence

<400> SEQUENCE: 1
```

-continued

```
Asp Glu Glu Phe Ala Leu Ala Ser His Leu Ile Glu Ala Lys Leu Glu
1               5                   10                  15

Gly His Gly Leu Pro Ala Asn Leu Pro Arg Arg Leu Val Pro Pro Ser
            20                  25                  30

Lys Arg Arg His Lys Gly Ser Ala Glu
        35              40
```

SYNTHETIC PEPTIDE, RELATIVE ARTIFICIAL ANTIGEN, RELATIVE ANTI-EHD2 ANTIBODY AND PREPARATION METHOD THEREOF AND USE THEREOF

This is a Continuation-in-Part of application Ser. No. 15/301,259 filed Sep. 30, 2016, which in turn is a National Phase of International Patent Application No. PCT/CN2014/082480 filed Jul. 18, 2014, which claims the benefit of Chinese Patent Application No. 201410125627.X filed Mar. 31, 2014. The disclosure of the prior applications is hereby incorporated by reference herein in its entirety.

FIELD OF THE INVENTION

The present invention relates to the biotechnology field, and more particularly it relates to a synthetic peptide, An artificial antigen, a method for preparing an antibody specific to a human EHD2 protein and adopted to detecting by an immunohistochemical method, an antibody specific to a human EHD2, a method of diagnosing and prognosing cancer.

BACKGROUND OF THE INVENTION

Breast cancer is one of the most common malignant tumors in women with an estimated incidence of about one million each year world widely. Since the late 1970s, the incidence rate of breast cancer has ranked first in tumors of female in China. North America and northern Europe used to be high incidence areas of breast cancer, but now also in China the incidence rate has grown from 17 per 100,000 to 52 per 100,000 in the last 5 years, showing a trend of rapid escalation, moreover, the age of onset is getting much younger than before, with the youngest being only 14 years old. Factors that trigger breast cancer could be various, in addition to genetic factors there exist other factors such as environmental conditions, mental health and working pressure et. al.

Furthermore, the incidence rate will be more higher in cities than that in rural areas. Nowadays, considerable efforts have been put in the world into investigating the occurrence and development of this disease, so as to adopt positive precautions.

At present, the method of discrimination of the degree of malignancy of tumors is mainly based upon conventional morphological observation performed on tumor tissues and tumor cells at the histopathological level in clinical practice, which is powerful in discriminating differentiation degrees and aggressive properties of cancer cells, with an accuracy of 50%-75%. However, this interpretation based on morphology is affected by human factors, such as experience of pathologists, and on the other hand, it lacks evidences at molecular level which may associated with individual patient's etiological factors, therefore, a combination with advanced molecular technologies is very necessary in order to increase the accuracy and specificity in tumor diagnosis, especially in providing theoretical evidences for individualized care including treatment protocol selection.

Although the occurrence of tumor is related to multiple factors, the primary one comes mainly from abnormal changes at the genetic level, including gene amplification, mutation, deletion and translocation, etc. which might lead to abnormal changes of multiple functional proteins in their expression, biological activities, and even subcellular distributions, and in case such changes endow cells with an uncontrollable proliferation property and failed to be reversed or killed by endogenous and exogenous protective mechanisms of a human body, tumor will emerge. Therefore, the premise for a deep understanding of the malignant nature of tumor and an effective control of the disease is to clarify the abnormal characteristics of these functional proteins, which requires the use of the approach of immunohistochemistry.

By using basic principles of antigen-antibody interactions in immunology, through specific recognition of antibodies to protein antigens in the body plus color development of secondary antibodies with chemical labelling (fluorophore, enzyme, metal ion, isotope and etc.), immunohistochemical techniques are employed to detect the expression quantity and subcellular localization of the target antigen (polypeptide and protein) in tissues and cells. In recent years, with the development of valuable specific antibodies, more importantly with the deep understanding of molecular mechanisms underlying tumors, the application value of immunohistochemistry in tumor molecular diagnosis has been well recognized. For example, estrogen receptor (ER), progesterone receptor (PR) and Her2 of the epidermal growth factor receptor family have been widely used in the clinically molecular pathological diagnosis of breast cancer, which plays an active role of guidance in pathological classification and clinical medication of breast cancer. These achievements are inseparable from the advance in basic cancer research, and it is expected that novel molecular markers will be further revealed and incorporated into clinical application, thus further improving our ability for tumor diagnosis and treatment. EHD2 gene and its encoded protein may be such new molecular markers.

EHD2 (Epsin 15 homology [EH]-domain-containing protein 2) is one of the EHD proteins that are members of a new family of membrane trafficking regulators, it contains a highly conserved EH domain which is composed of about 100 amino acid residues and was first discovered in EGFR Kinase substrate Eps15 (Epidermal Growth Factor Receptor Pathway Substrate Clone 15). EHD2 is involved in the regulation of multiple steps in cellular membrane transport, including internalization, transition between early endosomes and late endosomes and so on. The regulation of various steps on membrane and membrane proteins functions, including digestive degradation and recycling, takes an indispensable important part in cell biology, and cellular membrane trafficking plays a key role in maintaining the homeostasis of signal transduction and material transport in a variety of cellular processes, whereas the disruption of the balance will lead to improper signal responses, cell functional disorders and end up probably to diseases.

Chinese literature "*Effects of EHD2 Interference on Proliferation and Migration of Immortalized Breast Epithelial Cells HBL100*" (WANG Hongyu, et al. *Chinese Journal of Clinical Oncology*, 2011, 38(11)) disclosed a lower expression level of EHD2 in breast carcinoma, suggesting that EHD2 might be inhibitory to breast tumor progression. However, it is found from a further immunohistochemical study that although the overall quantity of expression of EHD2 tends to decrease, this trend mainly occurs in the nuclei; on the contrary, its expression level in cytoplasms tends to increase. Moreover, the expression level of EHD2 in nuclei is closely related to the survival condition of patients. Therefore, immunohistochemical detection of EHD2 will help more objectively and accurately reveal an alienated nature of tumors and clinical prognosis conditions of an individual patient.

There are over ten commercial antibodies against EHD2 available, which are provided by major biotech companies such as Santa Cruz and Abcam, but all these antibodies are for basic research only, and there is no evidence suggesting that these antibodies, like ours, have qualified specificity and can be used for immunohistochemical detection, especially at present there is still no other antibodies to EHD2 that are verified by means of immunohistochemistry on a large number of clinical tissue samples and there are no results available showing that the detection of abnormal subcellular localization of EHD2 can be used and valuable for tumor diagnosis and predicting prognosis. Compared with the antibody in the present application, the commercial ones have the following defects:

1. According to common knowledge in the art, as for antibodies which can be used for immunohistochemistry (IHC), clear indication and instruction of use will be provided in their user manuals. Therefore, most of the commercial antibodies have no such indications or instructions and cannot be used for immunohistochemical (IHC) detection. Although for some antibodies immunohistochemistry (IHC) is included in the indication, but it is found not really correct after careful check. One is an EHD2 antibody authorized to be sold by Nanjing SenBeiJia Biological Technology Co., Ltd., but the antibody is indicated only for membrane localization detection. The other is an antibody with the item No. 11440-1-AP from Proteintech, but the antibody has some problems in specificity: first of all, the strongest signal band detected by immunoblotting is at 60 kD, significantly smaller than the right 70 kD, whereas the 70 kD signal is much weaker, suggesting that although this antibody is able to detect EHD2, it actually will detect more strongly other unknown proteins; secondly, from the provided immunohistochemistry (IHC) images for lung cancer tissues it is found that the antibody staining is primarily nonspecifically on the mesenchymal region.

2. All these antibodies are reagents for research use, are not tested or verified by using a large cohort of clinical tissue samples, and not able to detect the nuclear localization of EHD2, therefore, these antibodies cannot meet the requirement for tumor diagnosis and survival prognosis by nuclear detection of EHD2 protein.

3. No strict specificity test of those antibodies was performed by immunoblotting assay, especially it lacks the verification of cross-reactions of the antibodies to EHD1, EHD3 and EHD4 proteins which are highly homologous to EHD2 protein, and this type of specificity test is very crucial for immunohistochemical detection of EHD2, due to the high homology between EHD proteins (>70%).

Chinese literature "*Down-regulation of EHD2 Enhanced Transformed Growth of Breast Epithelial Cell*" (TIAN Gang, et al. *Journal of Modern Laboratory Medicine*, 2012, 27(1): 49-51) disclosed a self-made antibody to EHD2, which is prepared by using our method for antibody generation without antigen purification, it can be used for immunoblotting but not qualified for IHC.

Currently, no commercial EHD2 antibody is tested for nuclear EHD2 expression and through a large number of clinical tissue specimens, so it is impossible for them to obtain a technical solution related to the present application, that is the current EHD2 antibodies are not suitable for nuclear localization detection of EHD2 and therefore cannot be used to evaluate the malignancy nature of cancer or the survival prognosis of patients.

SUMMARY OF THE INVENTION

In order to solve the current problem: the lack of commercial antibody adopted for EHD2 immunohistochemical detection, especially the lack of an antibody capable of detecting EHD2 protein expression levels in the nucleus of tissue samples, this application provides an antibody specific to a human EHD2 protein by using a synthetic peptide, an artificial antigen, a method for preparing an antibody specific to a human EHD2 protein and adopted to detecting by an immunohistochemical method and further provide a method of diagnosing or prognosing cancer by adopting the antibody of claim 5 to conduct a detection and quantification of nuclear EHD2 protein expression in human tissue samples, thus evaluate the malignancy degree of cancer or the survival prognosis of patients according to the results of the detection.

It is found from the immunohistochemical studies that in normal epithelium cells EHD2 is primarily distributed in cell nucleus and with lower level in cytoplasm and plasma membrane. However, in breast cancer tissues, the localization of EHD2 changes abnormally, with the trends of drop off in the nuclei whereas elevate up in the cytoplasm and plasma membrane. After a cohort IHC study by using clinical tissue samples, it is showed that the nuclear distribution of EHD2 is closely related to the survival condition of patients, that is, the lower the nuclear expression is, the worse the survival status of patients will be. These discoveries show that the malignant degree of breast cancer is closely associated with the extents of abnormal changes in the location and level of expression of EHD2 proteins in cancer cells in tissue, and immunohistochemical techniques are the only reliable means to detect the extents of such disorders of expression. Therefore, a problem to be solved in the prior art is to provide a method for detecting the expression conditions of expressed products of EHD2 gene at different locations inside cancer cells, especially in nuclei.

In order to solve the above-mentioned problem, the present invention provides the following technical means and solutions:

A synthetic peptide, wherein the synthetic peptide possesses an amino acid sequence as indicated by SEQ ID NO: 1 and plus a cysteine at its N-terminal, and SEQ ID NO: 1 is a fragment of EHD2 protein of 543 amino acids in length, and the synthetic peptide has 42 amino acids.

An artificial antigen, wherein the artificial antigen is the synthetic peptide coupling an antigen carrier.

Preferably, the antigen carrier is KHL.

A method for preparing an antibody specific to a human EHD2 protein and adapted to be detected by an immunohistochemical method, comprising conducting an animal immunization with the artificial antigen to obtain an antiserum, and subjecting the antiserum to affinity purification.

An antibody specific to a human EHD2, wherein the antibody is obtained by the method.

Preferably, the antibody is a polyclonal antibody.

Preferably, the antibody is chemically modified to add various enzymes or chromogenic groups, such as alkaline phosphatase and various fluorochromes, for direct detection of EHD2 protein.

A method of diagnosing or prognosing cancer, comprising localization and quantification of EHD2 protein expression in nuclei of human tissue cells by using the antibody.

Preferably, the cancer is a breast cancer.

Preferably, in a result of the localization and quantification of EHD2 protein expression in nuclei, the level of EHD2 protein expression in nuclei is negatively correlated with a malignancy degree of a tumor, but is positively correlated with a survival prognosis of a patient.

Preferably, the detection of location and quantification of EHD2 protein expression in nuclei comprising, using the antibody as a primary antibody to recognize EHD2 protein in human tissues, and using a secondary antibody or other reagents to obtain the readout of location and quantification of EHD2 protein expression in nuclei in human tissue cells.

Preferably, the detection of location and quantification of EHD2 protein expression in nuclei comprising, labeling the antibody and then directly detecting EHD2 protein expression in nuclei in human tissue cells without requiring a secondary antibody or other reagents.

An antibody specific to a human EHD2 protein, characterized in that the antibody is able to specifically recognize a human EHD2 protein, and the amino acid sequence of the region of recognition is: SEQ ID NO:1.

Use of EHD2 gene and its coded protein in diagnosis and prognosis of breast cancer by an immunohistochemical method, wherein an internationally universal sequence ID number for the EHD2 gene in GeneBank is: NM_014601, an internationally universal sequence ID number for the protein encoded by the EHD2 gene in GeneBank is: NP_055416.

The use of EHD2 gene and its coded protein in diagnosis and prognosis of breast cancer by the immunohistochemical method, characterized by using the aforementioned antibody.

Use of EHD2 gene and its coded protein in the preparation of a reagent for diagnosis and prognosis of breast cancer by an immunohistochemical method, wherein an internationally universal sequence ID number for the EHD2 gene in GeneBank is: NM_014601.

The use of EHD2 gene and its coded protein in the preparation of a reagent for diagnosis and prognosis anticipation of breast cancer by an immunohistochemical method, characterized by using the aforementioned antibody.

A polypeptide, characterized in that an amino acid sequence for the polypeptide is SEQ ID NO: 1.

Preferably, the polypeptide undergoes a modification with the aforementioned amino acid sequence as the core sequence, wherein the modification is achieved by adding a cysteine to the N-terminal of the polypeptide.

Use of the polypeptide in the preparation of the aforementioned antibody. Preferably, the polypeptide is used as an antigen to prepare an antibody to EHD2 by an immunization in animals.

The use of the polypeptide in the preparation of the antibody specific to the EHD2 protein. Preferably, the use is to perform antigen purification of the antibody.

An immunohistochemical reagent for diagnosis and prognosis evaluation of breast cancer, characterized by using the aforementioned antibody specific to the human EHD2 protein as primary antibody or core antibody.

The human EHD (EH domain-containing) protein family includes four members, EHD1, EHD2, EHD3 and EHD4, which is a novel type of membrane transport regulatory proteins with more than 70% sequence conservation. EHD2 is one of the above four EHD proteins involved in cell biological processes such as intracellular membrane and endosomal transport. Previously the applicant found that the protein expression level of EHD2 in human breast cancer cell lines appears to decrease, suggesting that EHD2 gene may be a new breast tumor suppressor gene, so it is necessary to test the expression of EHD2 in breast tissues and study its relationship with tumors.

In the present application, after extensive designing, screening and experimental verification, the applicant discloses a novel artificial antigen as well as an antibody generated by the antigen that is qualified for immunohistochemical detection of EHD2 on tissue samples and at a single cell level. By collecting a cohort of clinical breast samples and conducting IHC analysis, applicants found that the level of EHD2 expression in the nucleus detected by this method can reflect the malignancy degree of the tumor and the survival condition of the patients, which is however not reflected by the expression in the cytoplasm. Therefore, the expression level of EHD2 in the nucleus can be considered as a new marker and prognosis indicator for breast cancer, and such immunohistochemistry detection method has a prospect of use in clinical application.

The key of success of the immunohistochemistry technology is ultimately depending upon antibody, for IHC grade antibody must be highly qualified not only in specificity, but also in sensitivity and tissue sample compatibility. Although immuno-detection methods including immunohistochemistry, immunoblotting, flow cytometry and ELISA are based on the same principle of immunological antigen-antibody reaction, these technologies are different at the requirements for antibody qualities. For example, in immunoblotting approach, since the proteins are separated according to their molecular weight by electrophoresis, the quality requirement for antibody specificity is therefore not so stringent, because the proteins can also be distinguished by size. For flow cytometry and ELISA, specificity is important, however the sensitivity requirement of antibodies may be compromised because it can be compensated by antibody dilution and parameter adjustment on the instrument. However, as an immunohistochemistry IHC-grade antibody, it requires not only high specificity and sensitivity, due to a single cell detection, but also has to be able to recognize cross-linked target protein in the chemically fixed tissue. Only the antibody which meets these three criteria simultaneously can be used for immunohistochemistry.

In the Specification of the present invention, the following terms will be used:

"Protein encoded by EHD2 gene" means "EHD2 protein". It should be appreciated for those skilled in the art that when "expression of EHD2" is mentioned in the Specification, it means "expression of EHD2 gene and its coded protein".

"Core sequence" refers to the amino acid sequence from position 503 to 543 in human EHD2 protein (the protein number in GeneBank is NP_055416), after chemical synthesis or recombinant expression, the resultant polypeptide fragment corresponding to the core sequence, with or without modification, can be used for immunization to produce the antibody specific to EHD2 protein.

"Modification" means that the polypeptide fragment corresponding to the above-mentioned core sequence undergoes amino acid introduction, group coupling or purification adopting common methods such as a chemical process and recombinant DNA technique, for the purpose of being used for immunization to produce the antibody or antigen purification of the antibody.

It is found from the study that expression distribution of expressed products of EHD2 gene shows a trend of disorder in expression distribution if mammary epithelial cells become cancerous, and its extent of disorder, especially the expression condition in nuclei, is closely related to the survival condition of patients, and the detection using immunohistochemical techniques and artificial interpretation of results from the above detection are the only reliable means to learn the extent of expression disorder of this gene at different locations inside cells. However, most of the existing antibodies to EHD2 cannot be used for immunohistochemical detection, and there is no immunoblotting evidence showing that antibodies alleged to be able to be used for immunohistochemical detection have a qualified specificity, especially cross-reactions with homologous proteins of EHD2 protein cannot be excluded, in addition, it is found from the practical application that they may only react to the EHD2 protein in the cell membrane, while cannot recognize a valuable EHD2 protein in nuclei, or what they detect are just nonspecific signals from interstitial substance. Moreover, all the existing antibodies are not tested or statistically analyzed on the basis of a large sample size at the tissue level to show that they have the properties of recognizing the nuclear expression localization of EHD2 and the function of being used for prognosis anticipation. We provide an antibody specific to EHD2 with antigen purification and a use thereof in the preparation of an immunohistochemical detection reagent. The EHD2 antibody provided in the present invention has qualified specificity, it can specifically recognize the EHD2 protein, while cannot recognize other highly homologous proteins through testing using the immunoblotting method, and can quantitatively determine the EHD2 protein using the immunoblotting method, moreover, it can be prepared into an immunohistochemical reagent directly used for judging the expression and localization conditions of EHD2 in tissue cells, especially for monitoring the expression and localization conditions of EHD2 in the cell nucleus, thus better used for diagnosis and prognosis judgment of breast cancer.

The present application uses the antigen to immunize a rabbit to obtain a polyclonal antibody and perform antigen purification. The beneficial effects of the design is that the produced antibody not only has high specificity on EHD2, but also has high sensitivity that is capable to recognize EHD2 protein in a single cell nucleus, and can be applied in immunohistochemical techniques to detect chemically fixed and cross-linked EHD2 proteins in tissue samples. These effects are unattainable for commercial antibodies and therefore it is one of the major innovations of the present application.

The present application can realize the determination of tumor malignancy degree and the prognosis of the patients' survival, in particular, by collecting a large number of tumor clinical tissue specimens, applying the antibody of the present application for immunohistochemical detection, and then using the SPSS statistical software for conducting survival analysis of the detection results. Finally it is found the overall expression level of EHD2 cannot well reflect the malignancy degree of the tumor. However, after analyzing the expression level of EHD2 in the nucleus and cytoplasm, it is found that the level of EHD2 nuclear expression can reflect the malignancy degree of the tumor and the survival of the patients. These findings are another major innovation of the present application, and these are also important applications for the antigens and antibodies of the present application.

DETAILED DESCRIPTION OF THE EMBODIMENTS

Figure 1:
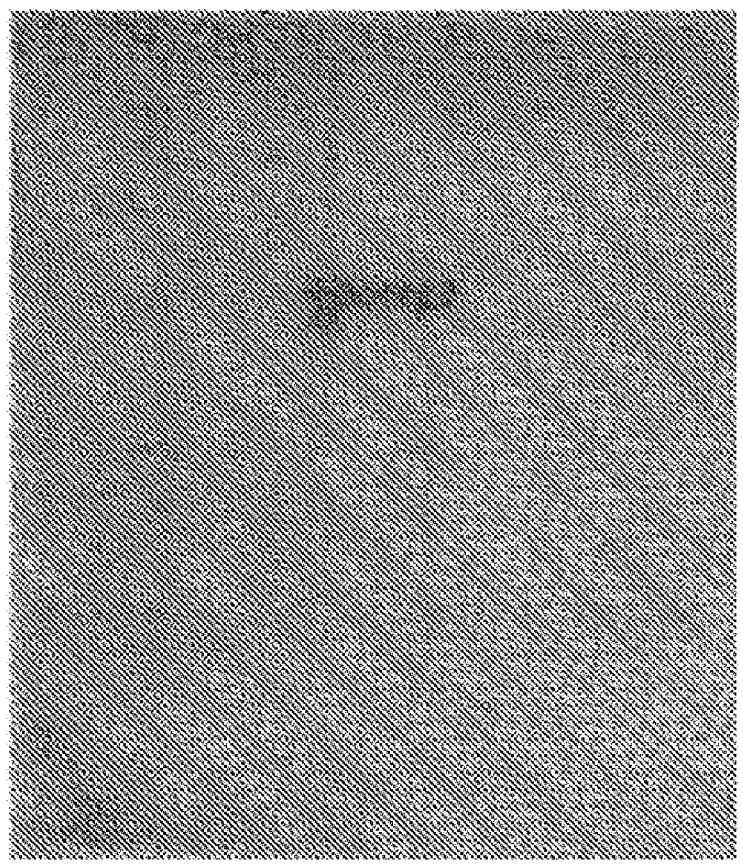
FIG. 1 shows an immunoblotting photo obtained from Example 1 of the specificity detection.
Figure 2:
FIG. 2 shows an immunohistochemical photo of normal tissue cells in Example 1 of an immunohistochemical detection.

The present invention will now be detailedly described by way of examples and with reference to the accompanying drawings.

Example 1 of an Antibody Preparation: Preparation of an Antibody Specific to EHD2

(1) Sources of Experimental Materials

New England white rabbits were purchased from China-Peptides Co., Ltd.; The polypeptide of CDEEFALASHLIEAKLEGHGLPANLPRRLVPPSKR-RHKGSAE (the polypeptide was obtained by modification with another polypeptide having an amino acid sequence of SEQ ID NO: 1 as a core sequence, and the modification method was adding a cysteine to its N-terminal) was custom-made by Tianjin Saier Biotechnology Co., Ltd. and was coupled with KLH.

CNBr-Activated gel beads, Freund's complete adjuvant and Freund's incomplete adjuvant were purchased from Invitrogen.

(2) Animal Immunization

Three four-month-old New Zealand white rabbits were taken for the study, 100 μg of an antigen polypeptide was dissolved in 0.2 ml of 0.1 M PBS (pH 7.2), the obtained solution was thoroughly mixed with an equal volume of Freund's complete adjuvant, which was multi-point injected into the abdominal subcutaneous region of each rabbit. On day 15 and day 29 after the initial immunization, a booster immunization is given by using 100 μg of the polypeptide/ 0.2 ml of PBS thoroughly mixed with an equal volume of Freund's incomplete adjuvant, respectively.

(3) Preparation of an Antiserum Against EHD2

Blood was collected from a carotid artery one week after the last immunization, then kept still at 37° C. for 3 hours and centrifuged to get the serum.

(4) Preparation of Antigen Gel Beads

CNBr-Activated gel beads were soaked in 1 mM HCl for 30 min, and washed with a coupling buffer (containing 0.1 M of NaHCO$_3$ with pH=8.3, and 0.5 M of NaCl), then a reaction system was mixed according to a proportion of adding 1 ml of gel to per 1 mg of the polypeptide. After coupling at 4° C. overnight, the system was soaked in 1 M ethanolamine for 3 hours, then washed in a cross manner with a washing liquid 1 (containing 50 mM Tris, 1 M NaCl, pH 8.0) and a washing liquid 2 (containing 50 mM glycine, 1 M NaCl, pH 3.5) for a total of 8 times, followed by washing once with PBS.

(5) Purification of EHD2 Antibody

The serum was mixed with the above-mentioned antigen gel beads according to a volume proportion of 20:1 to get a mixed system, then an equal volume of PBS was added to the system, followed by mixing uniformly and one hour later taking centrifugation, the gel beads were washed with PBS and the antibody coupled to the gel beads was eluted with sodium citrate solution with pH=3, then the pH value was adjusted to 6.5-7.5, the a purified EHD2 antibody was finally obtained.

Example 1 of a Detection: Specificity Detection of EHD2 Antibody Using an Immunoblotting Method (1) Sources of Experimental Materials 293T cells were purchased from American Type Culture Collection (ATCC); culture medium RPMI 1940, BSA, HRP-labeled Anti-Rabbit Secondary Antibodies, Lipo2000 Transfection Reagent, RIPA lysis buffer, BCA protein concentration assay reagent, and ECL chemiluminescence assay reagent were all purchased from Invitrogen; EHD1, EHD2, EHD3 and EHD4 expression plasmids were self-made.

(2) Cell Culture 293T cells were cultured in the culture medium RPMI 1940, and were grown by adherent culture at 37° C. with 5% CO2; when the cells were passaged, firstly the culture medium was discarded, then the cells were washed twice with phosphate buffered saline (PBS), after that, 0.05% trypsin was added for digestion, 2 minutes later, the culture medium was added to stop the digestion. The cells were kept in good condition, and passed one generation every two days. At the time of transfection, the plasmids that express EHD1, EHD2, EHD3 and EHD4 and the transfection reagents were added, respectively, two days later, the cells were collected for immunoblotting experiments.

(3) Immunoblotting Method

Different cells in sufficient quantities were reserved in centrifuge tubes, after centrifugation the cells were lysed in RIPA lysis buffer, followed by boiling and another centrifugation so as to obtain samples. After the samples were made, their protein concentrations were determined by the BCA assay reagent. For each sample, 80 μg of total protein was taken for SDS-PAGE electrophoresis. When the electrophoresis was completed, the proteins in the gels were electrotransferred onto PVDF membranes, followed by blocking with 5% milk at room temperature for 1 hour. After washing, the membranes were incubated with a primary antibody (the antibody prepared in Example 1 was diluted 1/2000 in PBS containing 5% BSA) at room temperature for 1 hour. Next, the membranes were incubated with Anti-Rabbit Secondary Antibodies diluted 1/5000 at room temperature for 1 hour. Finally, the membranes were detected with the chemiluminescence assay reagent and the detection results were shown in FIG. 3. It can be seen from the figure that the antibody specific to EHD2 provided in the present invention is able to specifically recognize the EHD2 protein, while not able to recognize other homologous EHD proteins.

(4) Results

The antibody against EHD2 has the ability to specifically and immunologically recognize the EHD2 protein, whereas has no cross-reactions with other homologous proteins. The detection results were shown in FIG. 1, in FIG. 1, sample Ve is the a empty expression vector, no signal; sample No. 1 represents overexpression of EHD1 protein, no signal; sample No. 2 represents overexpression of EHD2 protein, there appears a main band at the location corresponding to a molecular weight of 70 KD, the signal is clear and there is no other obvious background bands; sample No. 3 represents overexpression of EHD3 protein, no signal; and sample No. 4 represents overexpression of EHD4 protein, no signal. In conclusion, the antibody provided in this example can produce the intensive signal at the right location of 70 KD, whereas cannot produce signals at other locations, these results show that the antibody provided in the present invention has perfect specificity.

Example 1 of an Immunohistochemical Detection: Immunohistochemical Detection of EHD2

(1) Sources of Experimental Materials:

Breast cancer slices were obtained from the a tumor tissue bank of Tianjin Cancer Hospital, with routine conventional dewaxing. The total number of sample is 260. Diluent of the primary antibody, Horseradish Peroxidase (HRP)-labeled Universal Secondary Antibody, Diaminobenzidine (DAB) substrate, and Substrate Diluent Solution were purchased from ZSGB-BIO Co. Ltd.

(2) Preparation Conditions for Immunohistochemical Detection Reagents and Detection Methods for EHD2 Expression and Localization in Tissue Samples:

Main steps for the method are as follows: tissue slices were dewaxed until the wax had been replaced with water, then performed antigen retrieval and blockage of endogenous peroxidases. The antibody prepared from Example 1 was used as the primary antibody, and dropped inside at 1/200 dilution, incubated at 4° C. overnight. Samples were washed with buffer three times, 5 min for each time. The HRP-labeled universal secondary antibody was dropped inside for incubation at room temperature for 30 min. Samples were washed again with buffer three times, 5 min for each time. DAB staining, restaining, dehydration, and mounting were performed for staining observation under a microscope.

Figure 3:
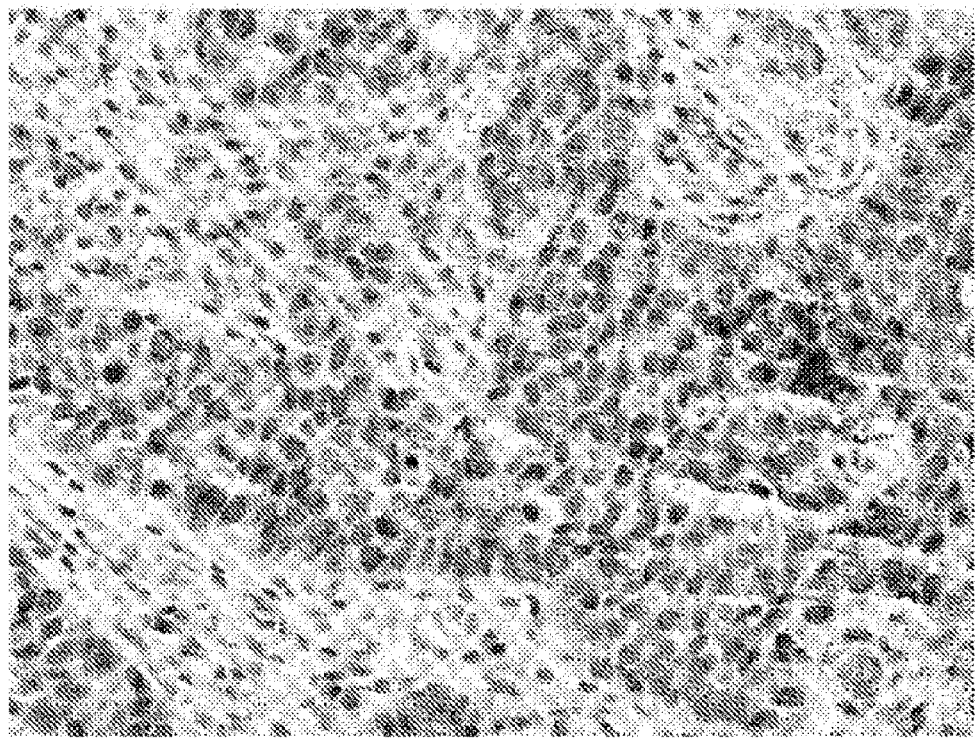
FIG. 3 shows an immunohistochemical photo of breast cancer cells in Example 1 of an immunohistochemical detection.
Figure 4:
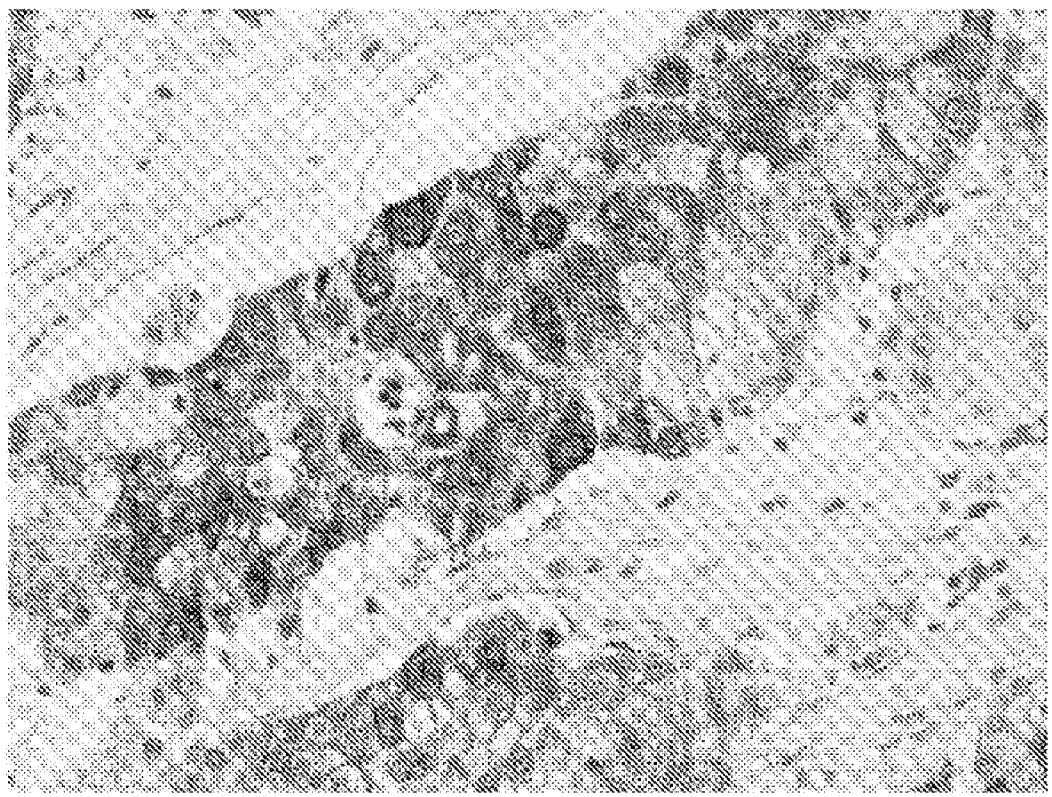
FIG. 4 shows an immunohistochemical photo of breast cancer cells in Example 1 of an immunohistochemical detection.
Figure 5:
FIG. 5 shows an immunohistochemical photo of breast cancer cells in Example 1 of an immunohistochemical detection.

(3) Results:

EHD2 expression in epithelial nuclei of normal tissues was positive, and the expression in the cytoplasm and membrane was weakly positive. In cancer tissues, EHD2 expression produced a disorder and the expression in nuclei tended to be weak. Typical immunohistochemical photos were shown in FIG. 2-FIG. 5, FIG. 2 was an immunohistochemical photo for normal tissues, showing that EHD2 was expressed in epithelial nuclei of normal cells, FIG. 3-FIG. 5 were immunohistochemical photos for different breast cancer tissue samples, in the breast cancer tissue sample as shown in FIG. 3, EHD2 was expressed both in cancer nuclei and cytoplasm, in the breast cancer tissue sample as shown in FIG. 4, EHD2 was not expressed in cancer nuclei, whereas was intensively expressed in the cytoplasm; in the breast cancer tissue sample as shown in FIG. 4, an overall loss of EHD2 expression was found in breast cancer cells, showing that the expression of EHD2 in cancer cells produced a disorder and the expression in nuclei was weakened. A progression-free survival curve of a total of 260 samples was shown in FIG. 6, and legends for the figure were as follows: 0 represented negative expression in nuclei; 1 represented positive expression in nuclei; censored represented death. The horizontal axis displayed progression-free survival months, and the vertical axis displayed a percentage of progression-free survival cases. It can be seen from the figure that the prognosis of the cases with negative expression in nuclei is apparently poorer than that of cases with positive expression.

The above experimental results indicate that the immunohistochemical detection method adopting the antibody provided in the present invention as the core reagent has an ability to favorably detect the expression quantity and localization of EHD2 in breast cancer tissue cells, so as to directly interpret the localization and expression conditions of EHD2 in nuclei of cancer cells in order to anticipate malignant degree of breast cancer and survival prospects of patients.

Example 2 of an Antibody Preparation: Preparation of an Antibody Specific to EHD2

1. Sources of Experimental Materials

New England white rabbits were purchased from China Peptides Co., Ltd.; The polypeptide of CDEEFALASHLIEAKLEGHGLPANLPRRLVPPSKR-RHKGSAE (the polypeptide was obtained by modification with another polypeptide having an amino acid sequence of SEQ ID NO: 1 as a core sequence, and the modification method was adding a cysteine to its N-terminal) was custom-made by Tianjin Saier Biotechnology Co., Ltd. and was coupled with KLH.

CNBr-Activated gel beads, Freund's complete adjuvant and Freund's incomplete adjuvant were purchased from Invitrogen.

2. Experimental Method (1) Design of a Synthetic Peptide and Preparation of an Artificial Antigen Protein Blast protein sequence analysis tool was used to analyze the human EHD2 Protein sequence (NP_055416). A total of 30 possible peptide fragments with different length combinations in different regions were selected and designed, which were synthesized and purified and coupled with KLH. Finally, the artificial antigen was obtained with an amino acid sequence SEQ ID NO: 1 added a cysteine at the N-terminal and coupling to an antigen carrier.

(2) Animal Immunization

Three four-month-old New Zealand white rabbits were taken for the study, 100 μg of an antigen polypeptide was dissolved in 0.2 ml of 0.1 M PBS (pH 7.2), the obtained solution was thoroughly mixed with an equal volume of Freund's complete adjuvant, which was multi-point injected into the abdominal subcutaneous region of each rabbit. On day 15 and day 29 after the initial immunization, a booster immunization is given by using 100 μg of the polypeptide/0.2 ml of PBS thoroughly mixed with an equal volume of Freund's incomplete adjuvant, respectively.

(3) Preparation of an Antiserum Against EHD2

Blood was collected from a carotid artery one week after the last immunization, then kept still at 37° C. for 3 hours and centrifuged to collect a supernatant to get the antiserum.

(4) Preparation of Antigen Gel Beads

CNBr-Activated gel beads were soaked in 1 mM HCl for 30 min, and washed with a coupling buffer (containing 0.1 M of $NaHCO_3$ with pH=8.3, and 0.5 M of NaCl), then a reaction system was mixed according to a proportion of adding 1 ml of gel to per 1 mg of the polypeptide. After coupling at 4° C. overnight, the system was soaked in 1 M ethanolamine for 3 hours, then washed in a cross manner with a washing liquid 1 (containing 50 mM Tris, 1 M NaCl, pH 8.0) and a washing liquid 2 (containing 50 mM glycine, 1 M NaCl, pH 3.5) for a total of 8 times, followed by washing once with PBS.

(5) Purification of EHD2 Antibody

The antiserum was mixed with the above-mentioned antigen gel beads according to a volume proportion of 20:1 to get a mixed system, then an equal volume of PBS was added to the system, followed by mixing uniformly and one hour later taking centrifugation, the gel beads were washed with PBS and the antibody coupled to the gel beads was eluted with sodium citrate solution with pH=3, then the pH value was adjusted to 6.5-7.5, the a purified EHD2 antibody was finally obtained.

Example 2 of a Detection: Specificity Detection of EHD2 Antibody Using an Immunoblotting Method (1) Sources of Experimental Materials 293T cells were purchased from American Type Culture Collection (ATCC); culture medium RPMI 1940, BSA, HRP-labeled Anti-Rabbit Secondary Antibodies, Lipo2000 Transfection Reagent, RIPA lysis buffer, BCA protein concentration assay reagent, and ECL chemiluminescence assay reagent were all purchased from Invitrogen; EHD1, EHD2, EHD3 and EHD4 expression plasm ids were self-made.

(2) Cell Culture 293T cells were cultured in the culture medium RPMI 1940, and were grown by adherent culture at 37° C. with 5% CO2; when the cells were passaged, firstly the culture medium was discarded, then the cells were washed twice with phosphate buffered saline (PBS), after that, 0.05% trypsin was added for digestion, 2 minutes later, the culture medium was added to stop the digestion. The cells were kept in good condition, and passed one generation every two days. At the time of transfection, the plasmids that express EHD1, EHD2, EHD3 and EHD4 and the transfection reagents were added, respectively, two days later, the cells were collected for immunoblotting experiments.

(3) Immunoblotting Method

Different cells in sufficient quantities were reserved in centrifuge tubes, after centrifugation the cells were lysed in RIPA lysis buffer, followed by treating for 5 min at 95 degree and another centrifugation to obtain the supernatant as samples. After the samples were made, their protein concentrations were determined by the BCA assay reagent. For each sample, 80 μg of total protein was taken for SDS-PAGE electrophoresis. When the electrophoresis was completed, the proteins in the gels were electrotransfered onto PVDF membranes, followed by blocking with 5% milk at room temperature for 1 hour. After washing, the membranes were incubated with a primary antibody (the antibody prepared in Example 1 was diluted 1/2000 in PBS containing 5% BSA) at room temperature for 1 hour. Next, the membranes were incubated with Anti-Rabbit Secondary Antibodies diluted 1/5000 at room temperature for 1 hour. Finally, the membranes were detected with the chemiluminescence assay reagent and the detection results were shown in FIG. 1.

(4) Results

The antibody against EHD2 has the ability to specifically and immunologically recognize the EHD2 protein, whereas has no cross-reactions with other homologous proteins. The detection results were shown in FIG. 1, in FIG. 1, sample Ve is the a empty expression vector, no signal; sample No. 1 represents overexpression of EHD1 protein, no signal; sample No. 2 represents overexpression of EHD2 protein, there appears a main band at the location corresponding to a molecular weight of 70 KD, the signal is clear and there is no other obvious background bands; sample No. 3 represents overexpression of EHD3 protein, no signal; and sample No. 4 represents overexpression of EHD4 protein, no signal. In conclusion, the antibody provided in this example can produce the intensive signal at the right location of 70 KD, whereas cannot produce signals at other locations, these results show that the antibody provided in the present invention has perfect specificity. Therefore, the antibody prepared by the antigen provided by the application can specifically identify EHD2 protein, while it does not cross-react the highly homologous EHD1, EHD3 and EHD4 proteins, which is not shown by all the commercial anti-EHD2 antibodies in the prior art.

Example 2 of an Immunohistochemical Detection: Immunohistochemical Detection of EHD2

(1) Sources of Experimental Materials:

Breast cancer slices were obtained from a tumor tissue bank of Tianjin Cancer Hospital. Diluent of the primary antibody, Horseradish Peroxidase (HRP)-labeled Universal Secondary Antibody, Diaminobenzidine (DAB) substrate, and Substrate Diluent Solution were purchased from ZSGB-BIO Co. Ltd.

(2) Preparation Conditions for Immunohistochemical Detection Reagents and Detection Methods for EHD2 Expression and Localization in Tissue Samples:

Main steps for the method are as follows: tissue slices were dewaxed until the wax had been replaced with water, then performed antigen retrieval and blockage of endogenous peroxidases. The antibody prepared from Example 1 was used as the primary antibody, and dropped inside at 1/200 dilution, incubated at 4° C. overnight. Samples were washed with buffer three times, 5 min for each time. The HRP-labeled universal secondary antibody was dropped inside for incubation at room temperature for 30 min. Samples were washed again with buffer three times, 5 min for each time. DAB staining, restaining, dehydration, and mounting were performed for staining observation under a microscope.

(3) Immunohistochemical Results:

EHD2 expression in epithelial nuclei of normal tissues or para-carcinoma tissues was positive, and the expression in the cytoplasm and membrane of cells was weakly positive. In cancer tissues, EHD2 expression produced a disorder and the expression in nuclei tended to be weak. Typical immunohistochemical photos were shown in FIG. 2-FIG. 5, FIG. 2 was an immunohistochemical photo for normal tissues, showing that EHD2 was expressed in epithelial nuclei of normal cells, FIG. 3-FIG. 5 were immunohistochemical photos for different breast cancer tissue samples, in the breast cancer tissue sample as shown in FIG. 3, EHD2 was expressed both in cancer nuclei and cytoplasm, in the breast cancer tissue sample as shown in FIG. 4, EHD2 was not expressed in cancer nuclei, whereas was intensively expressed in the cytoplasm; in the breast cancer tissue sample as shown in FIG. 4, an overall loss of EHD2 expression was found in breast cancer cells, showing that the expression of EHD2 in cancer cells produced a disorder and the expression in nuclei was weakened.

The results of this embodiment show that the anti-EHD2 polyclonal rabbit antibody generated by the artificial antigen of the application can well identify the EHD2 expression in tissue cells and detect the EHD2 expression in the nucleus of single cell, which is not shown by all commercial antibodies.

Example of breast cancer survival analysis: application of anti-EHD2 antibody generated by the antigen of the application in the determination of malignancy degree of breast cancer and prognosis of patients' survival.

(1) Sources of Experimental Materials:

260 cases of breast cancer formalin-fixed and paraffin-embedded specimens as well as the corresponding survival data of patients are from Tumor Tissue Bank of Tianjin Medical University Cancer Hospital.

(2) Experimental Method

The immunohistochemical method was the same as above Example 1.

The expression of EHD2 in the nucleus and cytoplasm of each specimen was examined, followed by conducting the survival analysis with SPSS statistical software.

(3) Results

Figure 6:
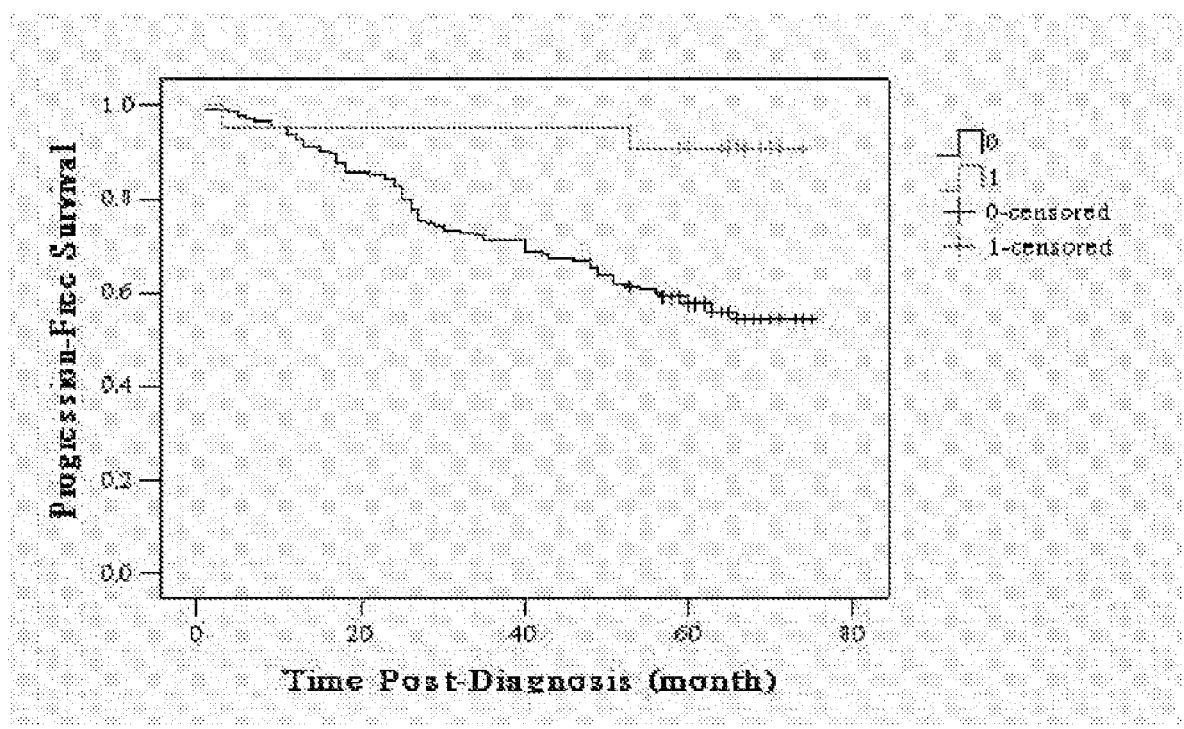
FIG. 6 shows a progression-free survival curve of a total of 260 samples in Example 1 of an immunohistochemical detection

A progression-free survival curve of a total of 260 samples was shown in FIG. 6, and legends for the figure were as follows: 0 represented negative expression in nuclei; 1 represented positive expression in nuclei; censored represented disease development and death. The horizontal axis displayed progression-free survival months, and the vertical axis displayed a percentage of progression-free survival cases. It can be seen from the figure that the progression-free survival of the cases with negative expression in nuclei is apparently poorer than that of cases with positive expression. The results of this experiment shows that the detection results of EHD2 expression in cell nucleus of breast cancer tissue samples can reflect the malignancy degree of breast cancer and survival prospect of patients.

The above experimental results indicate that the immunohistochemical detection method adopting the antibody provided in the present invention as the core reagent has an ability to favorably detect the expression quantity and localization of EHD2 in breast cancer tissue cells, so as to directly interpret the localization and expression conditions of EHD2 in nuclei of cancer cells in order to anticipate malignant degree of breast cancer and survival prospects of patients.

According to the detection results, the EHD2 protein expression in nuclei is negatively correlated with a malignancy degree of a tumor, i.e. the lower of the EHD2 protein expression in nuclei, the higher of the malignancy degree; and the EHD2 protein expression in nuclei is positively correlated with patient survival, i.e. the higher of the EHD2 protein expression in nuclei, the better of patient survival.

In this application, the antibody can also be chemically modified to add various enzymes or chromogenic groups, such as alkaline phosphatase, or various fluorophores, for direct detection of EHD2 protein.

In this application, the detection of EHD2 by localization and quantification of its expression in the nuclei comprises, labeling the antibody by chromophore or fluorophore and which then can be used for detection of EHD2 protein without requiring a secondary antibody or other reagents.

The invention claimed is:

1. A synthetic peptide consisting of the amino acid sequence of SEQ ID NO: 1 with a cysteine added at the N-terminal end.

2. An artificial antigen, wherein the artificial antigen is the synthetic peptide of claim 1 coupling an antigen carrier.

3. The artificial antigen according to claim 2, wherein the antigen carrier is KHL.

4. A method for preparing an antibody specific to a human Eps-15 homology domain-containing protein 2 (EHD2) and adapted to detect EHD2 by an immunohistochemical method, comprising:

administering to an animal an artificial antigen to obtain an antiserum, wherein the artificial antigen is a synthetic peptide coupling an antigen carrier, and the synthetic peptide consists of the amino acid sequence of SEQ ID NO: 1 with a cysteine added at the N-terminal end; and performing antigen affinity purification of the antiserum to isolate said antibody.

* * * * *